United States Patent [19]
Jones et al.

[11] Patent Number: 5,874,552
[45] Date of Patent: Feb. 23, 1999

[54] MODIFIED PHOSPHOROUS INTERMEDIATES FOR PROVIDING FUNCTIONAL GROUPS ON THE 5' END OF OLIGONUCLEOTIDES

[75] Inventors: David S. Jones; John P. Hachmann; Michael J. Conrad, all of San Diego; Stephen Coutts, Rancho Sante Fe; Douglas Alan Livingston, San Diego, all of Calif.

[73] Assignee: La Jolla Pharmaceutical Company, San Diego, Calif.

[21] Appl. No.: 436,100

[22] Filed: May 8, 1995

Related U.S. Application Data

[62] Division of Ser. No. 335,687, Nov. 8, 1994, which is a division of Ser. No. 915,589, Jul. 15, 1992, Pat. No. 5,391,785, which is a continuation-in-part of Ser. No. 731,055, Jul. 15, 1991, abandoned, which is a continuation-in-part of Ser. No. 494,118, Mar. 13, 1990, Pat. No. 5,162,515, which is a continuation-in-part of Ser. No. 466,138, Jan. 16, 1990, abandoned.

[51] Int. Cl.$^6$ .......................... C07H 19/00; C07H 21/00; C07H 21/02; C07H 21/04
[52] U.S. Cl. .................. 536/22.1; 536/23.1; 536/24.3; 536/25.3
[58] Field of Search .................. 536/22.1, 25.3

[56] References Cited

U.S. PATENT DOCUMENTS

| | | |
|---|---|---|
| 2,028,403 | 1/1936 | Mares . |
| 2,362,326 | 11/1944 | Thurston et al. . |
| 2,585,884 | 2/1952 | Whetstone et al. . |
| 2,619,493 | 11/1952 | Norris . |
| 2,946,806 | 7/1960 | Nentwig et al. . |
| 3,004,894 | 10/1961 | Johnson et al. . |
| 3,201,420 | 8/1965 | Fuzesi et al. . |
| 3,225,063 | 12/1965 | D'Alelio . |
| 3,308,064 | 3/1967 | Schlight et al. . |
| 3,926,912 | 12/1975 | Mayer-Mader et al. . |
| 4,058,550 | 11/1977 | Shepard et al. . |
| 4,191,668 | 3/1980 | Katz . |
| 4,220,565 | 9/1980 | Katz . |
| 4,465,869 | 8/1984 | Takaishi et al. . |
| 4,500,707 | 2/1985 | Caruthers et al. ................ 536/27 |
| 4,575,558 | 3/1986 | Mai et al. . |
| 4,588,824 | 5/1986 | Baldwin et al. . |
| 4,650,675 | 3/1987 | Borel et al. . |
| 4,751,181 | 6/1988 | Keene . |
| 4,845,219 | 7/1989 | Inoue et al. . |
| 4,877,891 | 10/1989 | Becker et al. . |
| 4,983,759 | 1/1991 | Inoue et al. . |
| 4,997,928 | 3/1991 | Hobbs . |
| 5,252,760 | 10/1993 | Urdea et al. . |
| 5,391,785 | 2/1995 | Jones et al. ........................ 522/105 |

FOREIGN PATENT DOCUMENTS

| | | |
|---|---|---|
| 0147768 | 2/1989 | European Pat. Off. . |
| 0354323 | 2/1990 | European Pat. Off. . |
| 0399330 | 11/1990 | European Pat. Off. . |
| 2326586 | 12/1973 | Germany . |
| 3937116 | 5/1991 | Germany . |
| 4-312541 | 11/1992 | Japan . |
| 110434 | 5/1964 | Norway . |
| WO 85/03704 | 8/1985 | WIPO . |
| WO 86/04093 | 7/1986 | WIPO . |
| WO 87/02777 | 5/1987 | WIPO . |

OTHER PUBLICATIONS

Miller et al. Biochermistry 25:5092–5097(1986).
Robles et al. Tetrahedron Letters 32(34):4389–4392(1991).
Bonfils et al. Tetrahedron Letters 32(26):3053–3056(1991).
Asseline et al. Tetrahedron Letters 30(19):2521–2524(1989).
Asseline et al. Tetrahedron Letters 31(1):81–84(1990).
Asseline et al. Nucleic Acids Research 19(15):4067–4074(1991).
Zuckermann et al. Nucleic Acids Research 15(13):5305–5321(1987).
Agrawal et al., "Efficient methods for attaching non–radioactive labels to the 5' end of synthetic oligonucleotides" *Nucl. Acids Res.* (1986) 14(15):6227–6245.
Kremsky et al., "Immobilization of DNA via oligonucleotides containing an aldehyde or carboxylic acid group at the 5' terminus" *Nucl. Acids Res.* (1987) 15(7):2891–2909.

(List continued on next page.)

*Primary Examiner*—W. Gary Jones
*Assistant Examiner*—Ethan Whisenant
*Attorney, Agent, or Firm*—Morrison & Foerster LLP

[57] ABSTRACT

Phosphoramidites of the formula

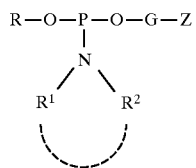

where R is a base-labile protecting group, $R^1$ and $R^2$ are individually alkyl of 1 to 6 carbon atoms, cycloalkyl of 3 to 8 carbon atoms, or aryl of 6 to 20 carbon atoms or are joined together to form with the nitrogen atom a cyclic structure of 4–7 carbon atoms and 0 to 1 annular chalcogen atoms of atomic number 8 to 16, G is a hydrocarbylene group of 1 to 20 carbon atoms and Z is a hydroxy-protected vicinal diol group bound to G by one of the vicinal diol carbon atoms or a disulfide group and bound to G by one of the sulfur atoms of the disulfide group, with the proviso that G is of at least 4 carbon atoms when Z is said disulfide group are used in conventional automated oligonucleotide synthesis to introduce a functional aldehyde or thiol group on the 5' end of the oligonucleotide to thereby provide a reactive site on the oligonucleotide that may be used to conjugate the oligonucleotide to molecules that contain a free amino group or an electrophilic center reactive with a thiol group.

18 Claims, 5 Drawing Sheets

OTHER PUBLICATIONS

Eshhar et al., "Induction of tolerance to nucleic acid determinants by administration of a complex of nucleoside D–glutamic acid and D–lysine (D–GL)" *J. Immunol.* (1975) 114(2):872–876.

Borel et al., "Prevention of murine lupus nephritis by carrier–dependent induction of immunologic tolerance to denatured DNA" *Science* (1973) 182:76–78.

Parker et al., "Modification of NZB/NZW $F_1$ autoimmune disease by development of tolerance to DNA" *J. Immunol.* (1974) 113(1):292–297.

Borel et al., "A possible new therapy of systemic lupus erythematosus (SLE)" *Ann. N.Y. Acad. Sci.* (1986) 475:296–306.

Papalian et al., "Reaction of systemic lupus erythematosus antinative DNA antibodies with native DNA fragments from 20 to 1,200 base pairs" *J. Clin. Invest.* (1980) 65:469–477.

Stollar et al., "Secondary structure in denatured DNA is responsible for its reaction with antinative DNA antibodies of systemic lupus erythematosus sera" *J. Clin. Invest.* (1980) 66:210–219.

Borel et al., "Oligonucleotide linked to human gammaglobulin specifically diminishes anti–DNA antibody formation in cultured lymphoid cells from patients with systemic lupus erythematosus" *J. Clin. Invest.* (1988) 82:1901–1907.

Mitsuo et al., "Preparation of lecithin–type of phospholipid analogues and mesomorphic states" *Chem. Pharm. Bull.* (1978) 26(5):1493–1500.

Gupta et al., "A general method for the synthesis of 3'–sulfhydryl and phosphate group containing oligonucleotides" *Chem. Abstracts* (1991) 115:976 (abstract No. 183758p).

U.S. Defensive Publication No. T909012 to McCollum (3 Apr. 1973).

Williams et al., "Stereocontrolled transformations of orthoester intermediates into substituted tetrahydrofurans" *J. Am. Chem. Soc.* (1984) 106(9):2641–2644.

Verkade et al., "Synthesen von glyceriden mit hilfe von tritylverbindungen IV" *Recl. Trav. Pays–Bas* (1940) 59:1123–1140.

Baggett et al., "Aspects of stereochemistry. Part XXI. Absolute configuration of benzylidene derivatives of some acyclic polyhydric alcohols" *J. Chem. Soc.* (1965) pp. 3394–3400.

Jackson et al., "Synthetic glycerides. IV. Esters of aromatic and aliphatic acids" *Am. Chem. Soc.* (1933) 55:678–680.

Fréchet et al., "Use of polymers as protecting groups in organic synthesis. III. Selective functionalization of polyhydroxy alcohols" *Can. J. Chem.* (1976) 54:926–934.

Ichikawa et al., "An asymmetric synthesis of glycerol derivatives by the enantioselective acylation of prochiral glycerol" *Chem Lett.* (1984) pp. 949–952.

Sedarevich, "Glyceride isomerizations in lipid chemistry" *J. Amer. Oil Soc.* (1967) 44(7):381–393. The corresponding Chemical Abstract, specifically *Chem. Abstract* (1967) 67:10965 (abstract No. 116524m), was previously submitted.

Shvets et al., "Lipids. LIX. Determination of the configuration of a β–diglycerides prepared from D–mannitol" *Zh. Org. Kihm.* (1968) 4(4):597–603. The corresponding Chemical Abstract, specifically *Chem Abstract* (1968) 69:231 (abstract No. 2454z), was previously submitted.

Hedgley et al., "Glycerol esters of thiobenzoic O–acids and thioglycerol esters of benzoic acid" *J. Chem. Soc.* (1970) pp. 467–471.

MODIFIED PHOSPHOROUS INTERMEDIATES FOR PROVIDING FUNCTIONAL GROUPS ON THE 5' END OF OLIGONUCLEOTIDES

CROSS-REFERENCE TO RELATED APPLICATIONS

This application is a divisional of application Ser. No. 08/335,687, filed Nov. 8, 1994, which is a divisional of Ser. No. 07/915,589, filed Jul. 15, 1992, now U.S. Pat. No. 5,391,783, which is a continuation-in-part of Ser. No. 07/731,055, filed Jul. 15, 1991, now abandoned, which is a continuation-in-part of Ser. No. 07/494,118, filed Mar. 13, 1990, now U.S. Pat. No. 5,168,515, which is a continuation-in-part of Ser. No. 07/466,138, filed Jan. 16, 1990 now abandoned.

DESCRIPTION

Technical Field

This invention is in the field of organophosphate chemistry and solid state oligonucleotide synthesis. More particularly, it concerns reactive phosphorous intermediates that may be stably attached to the 5' end of an oligonucleotide and which have an activatable moiety which, when activated, provides a functional aldehyde or sulfhydryl group that may be used to conjugate the oligonucleotide to any molecule having a free amino group.

Background

It is necessary to provide oligonucleotides with a free functional group in order to couple the oligonucleotide to labels, ligands, solid surfaces, polymers or other molecules or surfaces.

One technique for providing oligonucleotides with a terminal functional group involves synthesizing the desired oligonucleotide by conventional solid-state automated synthesis procedures and incorporating the functional group at the 5' end of the oligonucleotide via a modified phosphoramidite.

Agrawal, S., et al., *Nucl. Acids Res.* (1986) 14:6227–6245, describes a modified phosphoramidite that may be introduced on the 5' end of an oligonucleotide that has an activatable group that may be activated through deprotection to provide a free amino group on the 5' terminus of the oligonucleotide. The linker (VIII on page 6236), O-(2-(9-fluorenylmethoxycarbonyl) amino-ethyl)-O-(2-cyanoethyl)-N-N-diisopropyl. phosphoramidite, is added to the end of the desired oligonucleotide on an automated DNA synthesizer using deoxynucleoside-2-cyanoethyl-N-N-diisopropyl phosphoramidites. The adduct is deprotected (the 9-fluorenylmethoxycarbonyl group is removed with ammonia) to provide a free amino group.

Kremsky, J. N., et al., *Nucl. Acids Res.* (1987) 15:2891–2909, describes a functionalized phosphoramidite (1 on page 2893) that is introduced onto the 5' end of an oligonucleotide and then modified to provide a 5' carboxy or aldehyde group that is used to immobilize the oligonucleotide.

Another functionalized phosphoramidite, O-6-(4',4"-dimethoxytriphenylmethylthio)hexyl-O-(2-cyanoethyl)-N,N-diisopropylphosphoramidite, is available commercially from Clontech Laboratories. This molecule is incorporated into oligonucleotides using conventional phosphoramidite protocols. The dimethoxytrityl-protected sulfhydryl group may be deprotected with silver nitrate to yield a free sulfhydryl at the 5' end of the oligonucleotide chain.

A principal object of the present invention is to provide novel modified phosphorous intermediates that may be employed in the various types of oligonucleotide synthesis methods and which have activatable groups that may be converted to a free aldehyde or sulfhydryl group once they have been added onto the 5' end of an oligonucleotide. The free aldehyde/sulfhydryl group is useful for coupling or conjugating the oligonucleotide to labels, ligands, polymers or solid surfaces. These new intermediates meet the following criteria: 1) the. activatable group is compatible with all steps of conventional oligonucleotide synthesis procedures; 2) the activation is effected under conditions that do not damage the oligonucleotide; 3) the coupling is effected under conditions that do not damage the oligonucleotide or the moiety to which the oligonucleotide is coupled.

DISCLOSURE OF THE INVENTION

The novel phosphorus-containing compounds of the invention include intermediates that are useful in the H-phosphonate, phosphotriester, phosphorchloridite and phosphoramidite methods of oligonucleotide synthesis as well as intermediates that result in 5' modifications that involve phosphodiester analogs such as methyl phosphonates, methyl phosphates, phosphorothioates and phosphoramidates.

These compounds may be defined generically by the following formula where X is:
(i) oxygen when $X^1$ is $O^-$ and $X^2$ is hydrogen or RO- where R is a protecting group;
(ii) not present when
   (a) $X^1$ is chlorine and $X^2$ is methyl or RO-, or when
   (b) $X^2$ is RO- and $X^1$ is $NR^1R^2$ where $R^1$ and $R^2$ are individually alkyl of 1 to 6 carbon atoms, cycloalkyl of 3 to 8 carbon atoms, or aryl of 6 to 20 carbon atoms or are joined together to form with the nitrogen atom a cyclic structure of 4–7 carbon atoms and 0 to 1 annular chalcogen atoms of atomic number 8 to 16 inclusive (O or S);

G is a hydrocarbylene group of 1 to 20 carbon atoms; and

Z is a hydroxy-protected vicinal diol group bound to G by one of the vicinal diol carbon atoms or a disulfide group bound to G by one of the sulfur atoms of the disulfide group, with the proviso that G is of at least 4 carbon atoms when Z is said disulfide group.

The above compounds where X is oxygen, $X^1$ is $O^-$, and $X^2$ is hydrogen are H-phosphonates and are employed in the H-phosphonate method of oligonucleotide synthesis (Sinha and Cook, *NAR* (1988) 16:2659–2669). H-phosphonates may be converted to phosphite diesters, phosphorothioates, or phosphoramidates once they are incorporated onto the 5' end of the oligonucleotide (Miller et al., *NAR* (1983) 11:5189–5204, Eckstein, *Ann Rev Biochem* (1985) 54:367–402, and Froehler and Matteucci, *NAR* (1988) 16:4831–4839). Correspondingly, the above compounds where X is oxygen, $X^1$ is $O^-$ and $X^2$ is RO- are used in the phosphotriester approach to synthesizing oligonucleotides (Garegg, et al., *Chemica Scripta* (1985) 26:5). When X is not present and $X^1$ is chlorine and $X^2$ is RO-, the resulting compound is a phosphochloridite and it is used in the phosphochloridite technique for oligonucleotide synthesis (Wada et al., *J Org Chem* (1991) 56:1243–1250). The phosphoramidites of the above formula are preferred.

The preferred phosphoramidites of the invention may be represented by the formula:

(2)

where R is a base-labile protecting group, $R^1$ and $R^2$ are individually alkyl of 1 to 6 carbon atoms, cycloalkyl of 3 to 8 carbon atoms, or aryl of 6 to 20 carbon atoms or are joined together to form with the nitrogen atom a cyclic structure of 4–7 carbon atoms and 0 to 1 annular chalcogen atoms of atomic number 8 to 16 inclusive (O or S), G is a hydrocarbylene group of 1 to 20 carbon atoms and Z is a hydroxy-protected vicinal diol group bound to G by one of the vicinal diol carbon atoms or a disulfide group bound to G by one of the sulfur atoms of the disulfide group, with the proviso that G is of at least 4 carbon atoms when Z is said disulfide group.

Another aspect of the invention is a 5' modified oligonucleotide of the formula:

(3)

where (O.N.) represents an oligonucleotide chain, X is a chalcogen atom of atomic number 8 to 16, inclusive (O or S), $X^1$ is $O^-$, methyl, $-OCH_3$ or $NR^1R^2$ where $R^1$ and $R^2$ are individually hydrogen or alkyl of 1 to 6 carbon atoms, G is a hydrocarbylene group of 1 to 20 carbon atoms and Z is a hydroxy-protected vicinal diol group bound to G by one of the vicinal dial carbon atoms or a disulfide group bound to G by one of the sulfur atoms of the disulfide group, with the proviso that G is of at least 4 carbon atoms when Z is said disulfide group.

A further aspect of the invention is the above-described modified oligonucleotides where the hydroxy protecting groups have been removed to leave free hydroxyl groups.

Yet another aspect of the invention is the above-described 5'-modified oligonucleotide in which Z represents a deprotected vicinal diol group which has been oxidized to form a terminal aldehyde group on the oligonucleotide.

Another aspect of the invention is a conjugate of the above-described oligonucleotide having a terminal aldehyde group and a free amino group-containing carrier molecule wherein the conjugate is formed by reaction between the aldehyde group and the free amino group.

A further aspect of the invention is a partially protected trial of the formula:

(4)

where $Y^1$ and $Y^2$ are individual hydroxyl protecting groups or are joined by a single-atom bridge to form a five-membered ring protecting group, and G is described as above. Preferably G is alkylene of 4 to 20 carbon atoms.

Another aspect of the invention is a disulfide of the formula (5)

wherein $Y^3$ is a hydroxyl protecting group and G is as described above. The two divalent groups represented by G may be the same or different. Preferably they are the same, making the disulfide symmetrical. Preferably $Y^3$ is base stable. Preferably G is alkylene of 4 to 20 carbon atoms.

MODES FOR CARRYING OUT THE INVENTION

As indicated above, the phosphoramidites of the invention may be represented by the formula:

(2)

where R is a methyl or a base-labile protective group, $R^1$ and $R^2$ are alkyl of 1 to 6 carbon atoms, cycloalkyl of 3 to 8 carbon atoms, or aryl of 6 to 20 carbon atoms or are joined together to form with the nitrogen atom a cyclic structure of 4–7 carbon atoms and 0 to 1 annular chalcogen atoms of atomic number 8 to 16 inclusive (O or S), G is a hydrocarbylene group of 1 to 20 carbon atoms and Z is a hydroxy-protected vicinal diol group covalently bound to G via one of the vicinal carbon atoms or a disulfide group that is covalently bound to G via one of the sulfur atoms of the disulfide, provided that G is of at least 4 carbon atoms when Z is said disulfide group.

Preferably R is β-cyanoethyl, $R^1$ and $R^2$ are both isopropyl, and G is $-(CH_2)_n-$ where n is an integer from 4 to 6, inclusive. Examples of other protecting groups represented by R are β-nitroethyl, 2,2,2-trichloroethyl, methyl, 1,1-dimethyl-2,2,2-trichloroethyl, 2,2,2-tribromoethyl, benzyl, o-chlorophenyl, p-nitrophenylethyl, 2-methylsulfonylethyl, and 1,1-dimethyl-2-cyanoethyl. Examples of other groups which $R^1$ and $R^2$ may represent are other alkyl groups such as butyl, hexyl, nonyl, dodecyl, and hexadecyl, cycloalkyl groups such as cyclopropyl, cyclobutyl, cyclohexyl and cyclooctyl, aryl groups such as phenyl, tolyl, benzyl, xylyl and naphthyl, and when joined together heterocyclic groups such as morpholino, piperidinyl and thiomorpholino. Examples of other hydrocarbylene radicals which G may represent are branched alkylene, and groups containing cycloalkylene (e.g., cyclohexylene) or phenylene. It will be appreciated that G functions primarily as an inert spacer moiety and that it may have substituents and/or heteroatoms (e.g., O, S, N) in its structure that do not affect its ability to act as an inert spacer.

Preferred hydroxy-protected vicinal diol groups represented by Z are those of the formula:

where $R^3$ and $R^4$ are individually hydrogen, alkyl of 1 to 20 carbon atoms or monocyclic arylene of 6 to 20 carbon atoms and $Y^1$ and $Y^2$ are individual hydroxy-protecting groups or may be joined (designated by the dashed line) by a single-atom (C, S or Si) bridge to form a five-membered ring protecting group. $Y^1$ and $Y^2$ are of a nature that they are stable during the addition of the molecule to the 5' end of an oligonucleotide chain during chemical synthesis (i.e., conventional automated phosphoramidite synthesis) and can be removed thereafter without damaging the oligonucleotide chain. Further, as discussed below, the vicinal diol structure of the deprotected group permits it to be "activated" by oxidation to convert it from a diol to a functional aldehyde group. $Y^1$ and $Y^2$ may be the same or different and may be any of the individual hydroxy protecting groups that are compatible with conventional automated solid state oligonucleotide chemistry using phosphoramidite chemistry. Examples of such blocking groups are dimethoxytrityl (DMT), trityl, pixyl, benzoyl, acetyl, isobutynyl, p-bromobenzoyl, t-butyldimethylsilyl, and pivaloyl. The protecting groups may be removed with the same or different treatments. Such vicinal diol. groups in which $R^3$ and $R^4$ are hydrogen and $Y^1$ and $Y^2$ are benzoyl or DMT are particularly preferred.

As indicated, $Y^1$ and $Y^2$ may be linked by a one-atom bridge, thus forming a five-membered ring. Suitable bridging atoms include silicon, sulfur and carbon. It is preferred that the one-atom bridge be a carbon bridge. Thus, the diol group is preferred to be protected as an acetal or ketal, i.e., It is important that the bridging atom and its substituents be stable to the subsequent reactions in the sequence used to add the linker to the oligonucleotide. The diol protecting group must also be capable of being removed under mild conditions that do not substantially degrade the oligonucleotide. For example, very acidic conditions will lead to depurination of the oligonucleotide. Suitable groups $R^6$ and $R^7$ include aryl and substituted aryl groups of 6–30 carbon atoms, $C_1$–$C_{20}$ alkyl groups, and aromatic substituted alkyl groups of less than 30 carbon atoms. Preferred is phenyl and phenyl substituted with $C_1$–$C_8$ alkyl, $C_1$–$C_8$ alkoxy; 1 to 4 atoms of fluorine, chlorine, bromine, nitro- or phenyl. Most preferred are acetal structures wherein $R^6$ is phenyl, p-butylphenyl, p-methoxyphenyl, p-tert-butylphenyl; and biphenyl. It will be known to those skilled in the art that the stability of the protecting group can be adjusted for a particular use by a suitable choice of substituent(s).

The above-described acetals and ketals are easily prepared directly from the corresponding triols in one step. It is an important and unexpected feature of this embodiment of the present invention that the vicinal diol is selectively protected in the presence of another free alcohol in the molecule. Thus, the triol wherein $Y^1$ and $Y^2$ are H is simply contacted with an aldehyde to yield the acetal or a ketone to yield the ketal in the presence of an acid catalyst. It is preferred that the contacting take place under conditions where the water formed during the reaction is removed during the reaction, either by the application of vacuum or by solvent azeotrope. Alternatively, acetals or ketals of lower-boiling alcohols can be similarly employed in place of the aldehyde or ketone in an acetal exchange reaction.

The phosphoramidites of the above-described acetals and ketals are prepared by the conventional methods described herein, and they are coupled to the oligonucleotide during the synthesis, as is also described herein. Following the synthesis and purification of the free, coupled oligonucleotide, mild acid hydrolysis of the protecting group generates the diol that is the substrate for the oxidation reaction that produced the aldehyde used for the conjugation reaction. Typical mild hydrolysis conditions are 80% acetic acid/water at 25° C. for 30 minutes, similar to those used to remove a dimethoxytrityl group in conventional oligonucleotide synthesis.

Preferred disulfide groups represented by have the formula:

where $R^5$ is an alkylene group of 1 to 20 carbon atoms or a monocyclic arylene group of 6 to 20 carbon atoms and $Y^3$ is a hydroxy protecting group (as described above).

Most preferably $R^5$ is alkylene of 4 to 6 carbon atoms, —$OY^3$ is bound to the ω carbon atom of the alkylene group and $Y^3$ is trityl. As discussed below, the disulfide structure of the group permits it to be "activated" by reduction to cleave the disulfide bond and produce a free sulfhydryl group.

The phosphoramidites wherein Z represents a vicinal diol may be prepared from an alcohol of the formula HC=CH—G—OH. The hydroxyl group of the alcohol is protected and the double bond is oxidized to form the diol group. The hydroxyls of the diol are then protected with an orthogonally removable protecting group ($Y^2$ and $Y^3$), i.e., the protecting group on the original hydroxy can be removed without removing the protecting groups on the vicinal diol. The protecting group on the original hydroxy is then removed and the resulting deprotected hydroxy is reacted with an appropriate phosphitylating agent.

Figure 3:
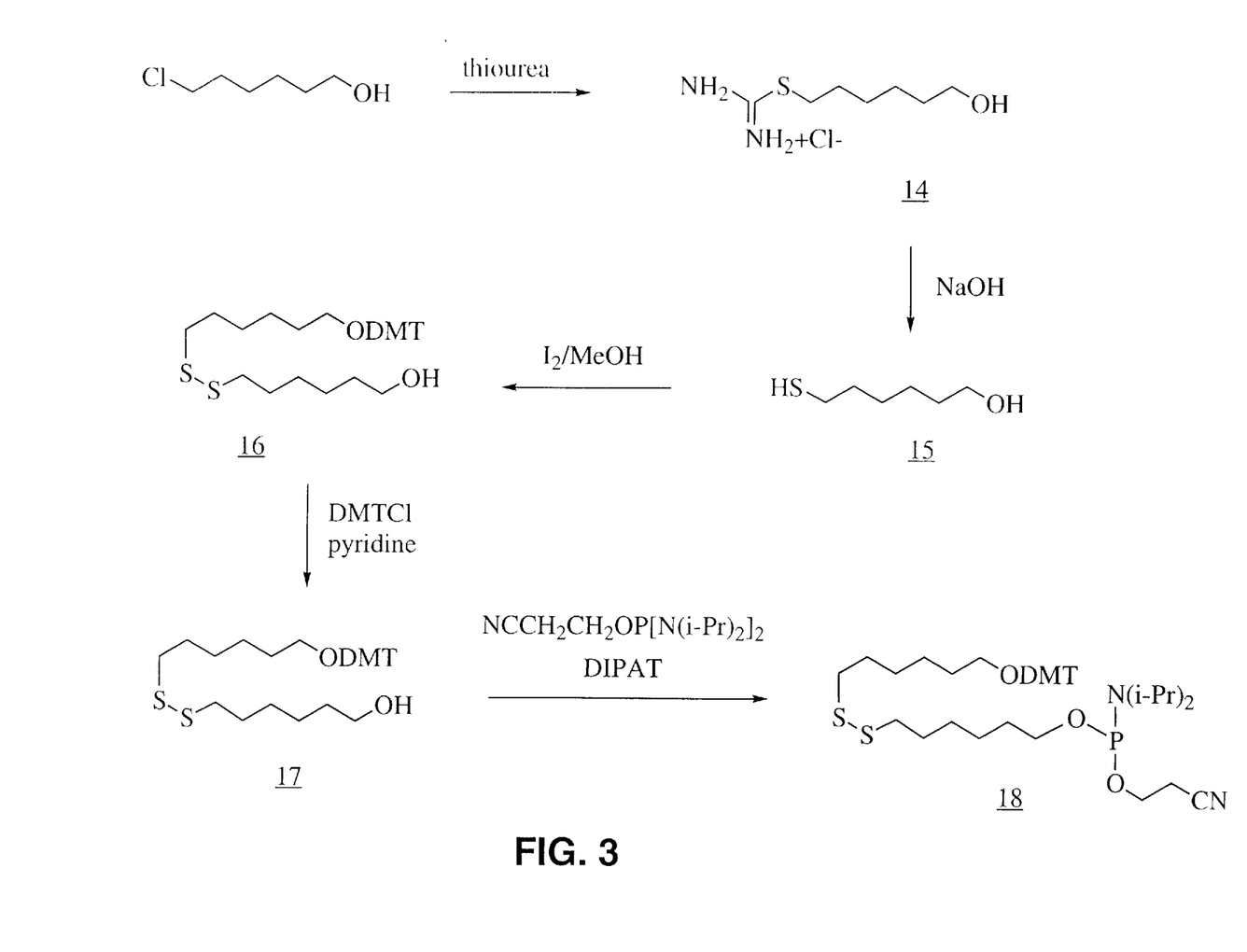

The phosphoramidites wherein Z represents a disulfide may be prepared from symmetrical or asymmetrical disulfides. The general reaction scheme employing symmetrical disulfides is shown in FIG. 3 and exemplified by Example 3, infra. Asymmetrical disulfides may be prepared as described by Mannervik, B., and Larson, K., *Meth. in Enzym.* (1981) 77:420–424, or Mukuiyama, T., and Takahashi, K., *Tet Lett* (1968) 5907–5908. By way of example, a symmetrical disulfide (HO—G—SS—G—OH) is oxidized with hydrogen peroxide and formic acid to provide the corresponding thiolsulfinate. Treatment of the thiolsulfinate with a mercaptan (e.g., HS—G'—$OY^3$ where $Y^3$ is as described above and G' is a different G than in the starting symmetrical disulfide) at a pH greater than 3 yields an asymmetrical disulfide (HO—G—SS—G'—$OY^3$). This disulfide may be reacted with a phosphitylating agent to yield the phosphoramidate.

The phosphoramidites of the invention may be added to the 5' end of an oligonucleotide chain using the conventional automated phosphoramidite method used to prepare oligonucleotides. See Matteucci, M. D., and Caruthers, M. H., *Tet Lett* (1980) 521:719, and U.S. Pat. No. 4,500,707. The oligonucleotide chain itself may be made by the same method. The length and sequence of the oligonucleotide to which the phosphoramidite of the invention is added will depend upon the use of the resulting 5'-functionalized oligonucleotide. For instance, if the oligonucleotide is to be used for the purposes described in parent application Ser. No. 494,118 (i.e., systemic lupus erythematosus (SLE) treatment), then the oligonucleotide will have the ability of bind SLE antibodies. If the oligonucleotide is to be used as a labeled probe then the length and sequence will be such as to be capable of hybridizing to a nucleotide sequence of interest.

As indicated above, the resulting modified oligonucleotide may be represented by the formula:

where (O.N.) represents an oligonucleotide chain and X, $X^1$, G and Z are as defined previously. The designation "5'" indicates that the modifying group is attached to the 5' end of the oligonucleotide chain. The chain will typically be 10 to 200 nucleotides in length, more usually 20 to 60 nucleotides in length.

Once the phosphoramidite has been added to the 5' end of an oligonucleotide chain, the protecting groups ($Y^1$, $Y^2$, $Y^3$) may be removed by appropriate treatment (e.g., base or acid treatment) to yield free hydroxy groups. In the case of the vicinal diol, the diol group is oxidized, e.g., with periodate, to form a terminal aldehyde group. In the case of the disulfide group, the disulfide is reduced with an appropriate reducing agent, e.g., a mercaptan such as dithiothreitol or 2-mercaptoethanol or borohydride to cleave the disulfide bond to form a terminal sulfhydryl group.

The resulting 5' modified oligonucleotide may be coupled via the aldehyde group to labels, carriers, or other molecules having a free amino group or via the sulfhydryl group to an electrophilic center such as maleimide or α-haloacetyl groups or other appropriate Michael acceptors such as acrylates or acrylamides. Examples of such carriers are amino acid polymers such as copolymers of D-lysine and D-glutamic acid, or immunoglobulin, or other polymers that inherently have been derivatized to include such groups as recited above.

EXAMPLES

The following examples further illustrate the invention. These examples are not intended to limit the invention in any manner. In the examples, Et=ethyl, Ac=acetyl, and THF=tetrahydrofuran.

Example 1

Figure 1:
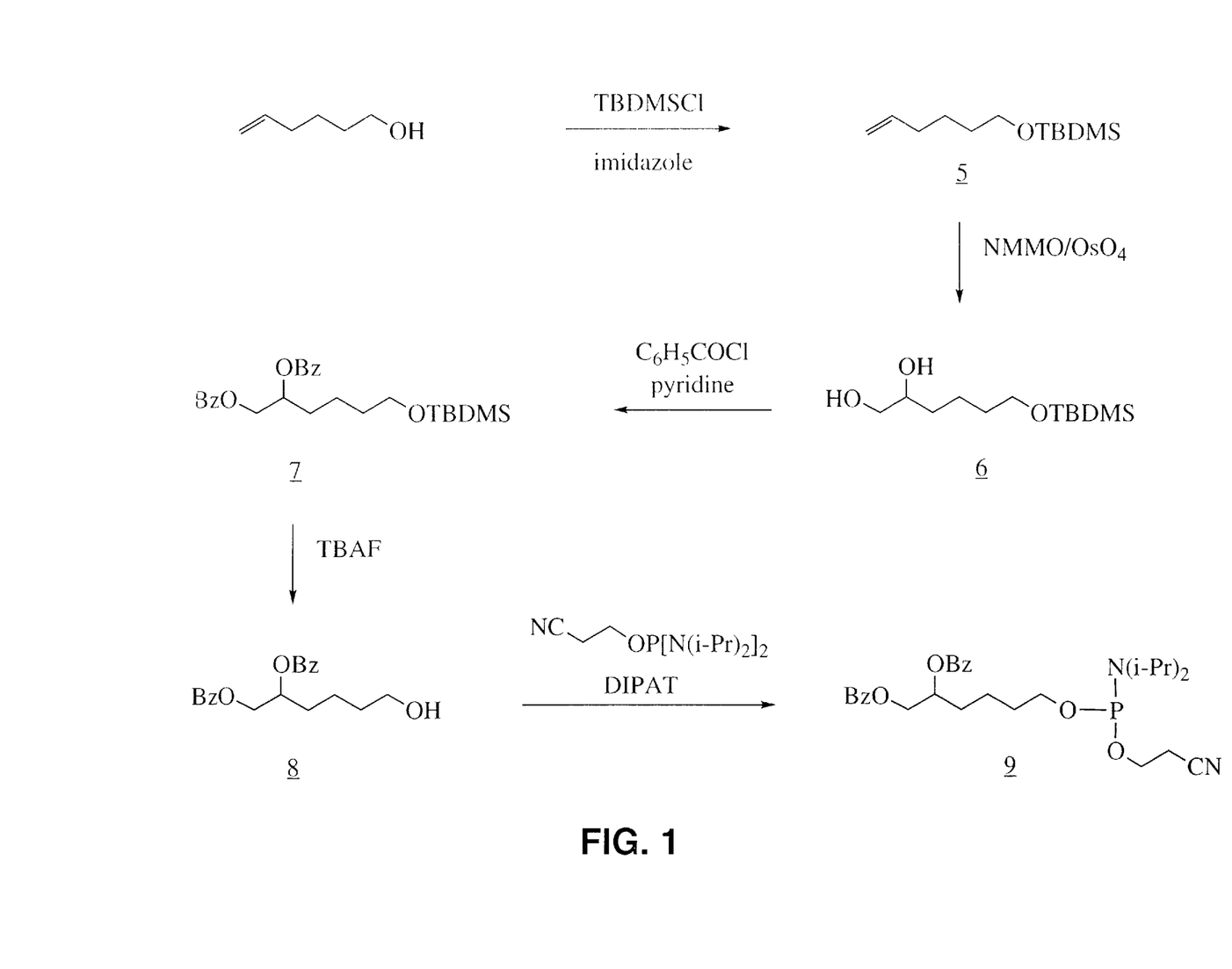
FIGS. 1–3 are schematic diagrams of the synthesis schemes described in Examples 1–3.

Preparation of O-(5,6-(bis-O-benzoyloxy)-hexyl)-O-(2-cyanoethyl)-N,N-diisopropylphosphoramidite FIG. 1 schematically depicts the invention scheme used to make this phosphoramidite. The details of this scheme are described below.

O-(tert-butyldimethylsilyl)-5-hexenol, 5. To a solution of 12.47 mL (10.4 g, 104 mmol) of 5-hexene-1-ol in 104 mL of DMF was added 15.66 g (230 mmol) of imidazole and 20.0 g (130 mmol) of tert-butyldimethylsilyl chloride (TBDMSCl). The mixture was stirred at ambient temperature for 4 hours and partitioned between 200 mL of EtOAc and 100 mL of saturated $NaHCO_3$ solution. The EtOAc layer was washed with 100 mL of saturated $NaHCO_3$ solution, 100 mL of saturated NaCl solution, dried ($MgSO_4$), filtered, and concentrated to a volume of approximately 100 mL. Distillation under vacuum provided 70.07 g of 5: bp 130°–143° C. @ 100 mmHg; $^1$H NMR ($CDCl_3$) 0.11 (s, 6H), 0.95 (s, 9H), 1.48 (m, 2H), 1.57 (m, 2H), 2.11 (dt, 2H), 3.66 (t, 2H), 5.03 (m, 2H), 5.86 (m, 1H); $^{13}$C NMR ($CDCl_3$) −5.25, 18.40, 25.21, 26.01, 32.35, 33.60, 63.09, 114.40, 138.92.

1-O-(tert-butyldimethylsilyl)-1,5,6-hexanetriol, 6. To a solution of 9.86 g (46.0 mmol) of 5 in 92 ML of acetone was added a solution of 6.46 g (55.2 mmol) of N-methylmorpholine oxide (NMMO) in 23 mL of $H_2O$. To the mixture was added 443 uL of a 2.5% solution of $OsO_4$ in tert-butyl alcohol (360 mg of solution, 9.0 mg of $OSO_4$, 35 μmol) and 50 uL of 30% $H_2O_2$. The mixture was stirred for 16 hours and a solution of 474 mg of sodium dithionite in 14 mL of $H_2O$ was added. After another 0.5 hour the mixture was filtered through celite. The filtrate was dried with $MgSO_4$ and filtered through 1" of silica gel in a 150 mL Buchner funnel using 250 mL portions of EtOAc to elute. Fractions containing product were concentrated to provide 11.0 g of 6 as a viscous oil: TLC $R_f$ 0.2 (1:1 hexane/EtOAc); $^1$H NMR ($CDCl_3$) 0.05 (s, 6H), 0.89 (s, 9H), 1.25 (m, 4H), 1.55 (m, 2H), 3.41 (dd, 2H), 3.62 (t, 2H), 3.71 (m, 1H); $^{13}$C NMR ($CDCl_3$) −5.23, 18.42, 21.91, 26.02, 32.68, 32.81, 63.16, 66.74, 72.24.

5,6-(bis-O-benzoyl)-1-O-(tert-butyldimethylsilyl)-1,5,6-hexanetriol, 7. To a solution of 5.29 g (21.3 mmol) of 6 in 106 mL of pyridine was added 6.18 mL (7.48 g, 53.2 mmol) of benzoyl chloride. The mixture was stirred for 18 hours and concentrated on the rotary evaporator. The mixture was partitioned between 100 mL of cold 1N HCl and 100 mL of EtOAc. The pH of the aqueous layer was checked to made sure it was acidic. The EtOAc layer was washed successively with 100 mL of $H_2O$ and 100 mL of saturated NaCl, dried ($MgSO_4$), filtered, and concentrated to provide 10.33 g of 7 as a viscous yellow oil; TLC $R_f$ 0.45 (1:4 EtOAc/hexanes); $^1$H NMR ($CDCl_3$) 0.05 (s, 6H), 0.88 (s, 9H), 1.59 (m, 4H), 1.85 (m, 2H), 3.14 (t, 2H), 4.49 (dd, 1H) 4.59 (dd, 1H), 5.54 (m, 1H), 7.45 (m, 4H), 7.58 (m, 2H), 8.05 (m, 4H).

5,6-(bis-O-benzoyl)-1,5,6-hexanetriol, 8. To a solution of 2.62 g (5.36 mmol) of 7 in 10.9 mL of THF was added 10.7 mL (10.7 nmol) of a 1N solution of tetrabutylammonium fluoride (CTBAF) in THF. The mixture was allowed to stir for 16 hours. The mixture was partitioned between 25 mL of saturated $NaHCO_3$ solution and 3×25 mL of EtOAc. The combined EtOAc extracts were washed with saturated NaCl solution, dried ($MgSO_4$), filtered and concentrated to a viscous oil which was purified by silica gel chromatography (1:1 hexane/EtOAc) to provide 823 mg of 8 as a viscous oil; $R_f$ 0.14 (1:1 hexane/EtOAc); $^1$H NMR ($CDCl_3$) 1.58 (m, 2H), 1.68 (m, 2H), 1.88 (m, 2H), 3.68 (t, 2H), 4.52 (dd, 1H), 4.62 (dd, 1H), 5.56 (m, 1H), 7.46 (m, 4H), 7.58 (m, 2H), 8.05 (m, 4H); $^{13}$C NMR ($CDCl_3$) 22.08, 31.20, 31.30, 32.88, 62.92, 66.17, 72.63, 128.93, 130.19, 130.57, 133.62, 166.72, 166.86.

O-(5-6-(bis-O-benzoyloxy)-hexyl)-O-(2-cyanoethyl)-N,N-diisopropylphosphoramidite, 9. To a solution of 1.02 g (2.98 mmol) of 8 and 255 mg (1.49 mg) of diisopropylammonium tetrazolide (DIPAT, prepared by mixing acetonitrile solutions of diisopropylamine and tetrazole in a one-to-one mole ratio and concentrating to a white solid) in 14.9 mL of $CH_2Cl_2$ was added a solution of 989 mg (3.28 mmol) of O-cyanoethyl-N,N,N',N'-tetraisopropylphosphorodiamidite in 2.0 mL of $CH_2Cl_2$. The mixture was stirred for 4 hours and partitioned between 25 mL of $CH_2Cl_2$ and 25 mL of chilled saturated $NaHCO_3$ solution. The $CH_2Cl_2$ layer was washed with saturated NaCl solution, dried ($Na_2SO_4$), filtered, and concentrated. Purification by filtration through a 2" plug of basic alumina in a 25 mm column, eluting with 9:1 EtOAc/$Et_3N$ provided 1.5 g (93%) of 9 as a viscous oil: $^1$H NMR ($CDCl_3$) 1.19 (m, 12H), 1.62 (m, 2H), 1.73 (m, 2H), 1.90 (m, 2H), 2.62 (dd, 2H), 3.53–3.92 (m, 6H), 4.53 (dd, 1H), 4.62 (dd, 1H), 5.58 (m, 1H), 7.48 (m, 4H), 7.60 (m, 2H), 8.09 (m, 4H); $^{31}$p NMR ($CDCl_3$ with 15% $H_3PO_4$ internal standard) 148.2; HRMS (FAB, MH$^+$), calculated for $C_{29}H_{40}O_6N_2P_1$ 543.2624, found 543.2619.

Example 2

Figure 2:
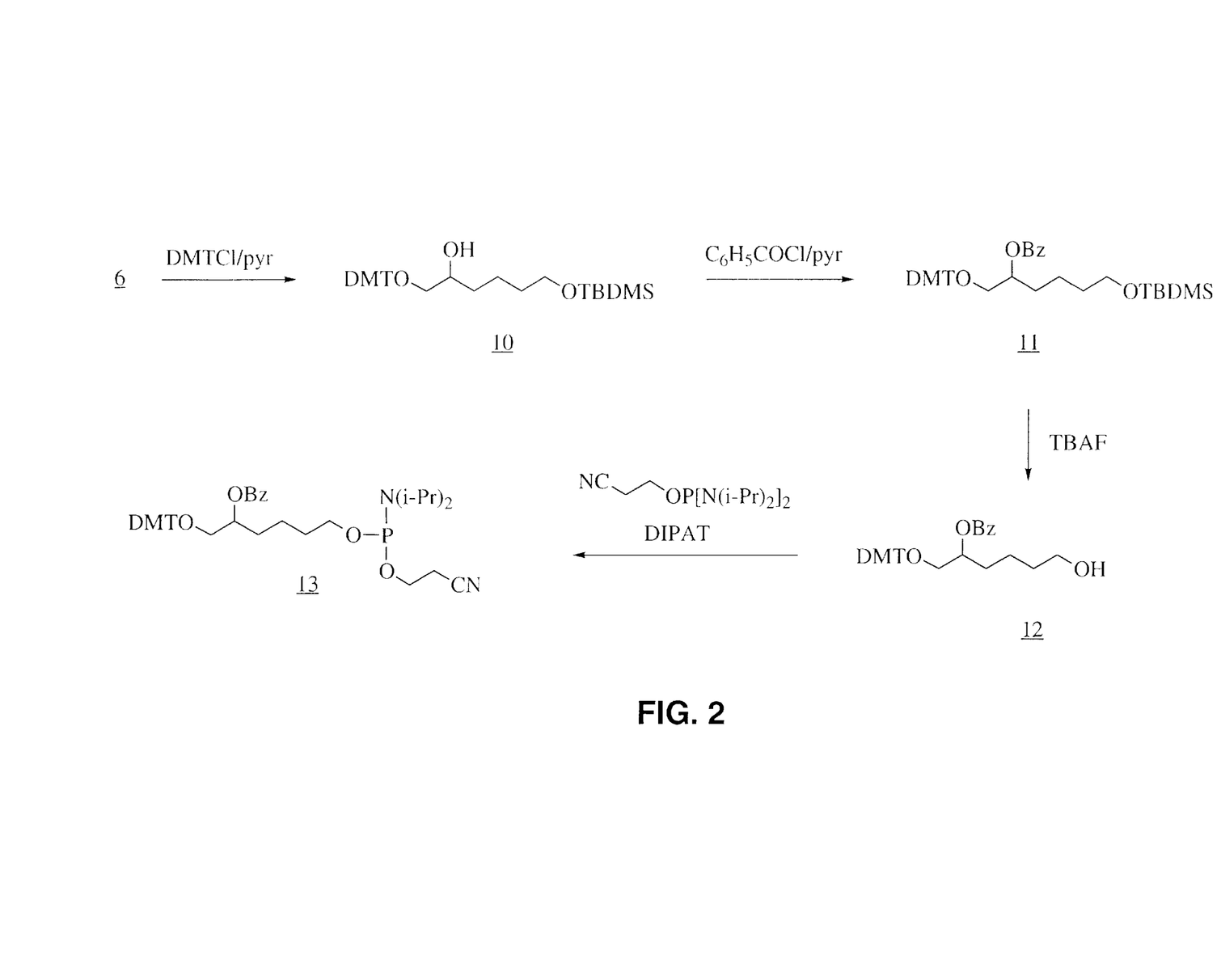

Preparation of O-5-benzyloxy-6-O-(4',4"-dimethoxytrityl) hexyl-O-(2-cyanoethyl)-N,N-diisopropylphosphoramidite FIG. 2 schematically depicts the reaction scheme for making this phosphoramidite. The details of the scheme are described below.

6-O-(4',4"-dimethoxytriphenylmethyl)-1-O-(tert-butyldimethylsilyl)-1,5,6-hexanetriol, 10. To a solution of 1.11 g (4.47 mmol) of 6 and 891 uL (638 mg, 6.30 mmol) of $Et_3N$ in 22 mL of pyridine was added 1.81 g (5.33 mmol) of 4,4'-dimethoxytriphenylmethyl chloride. The mixture was stirred at ambient temperature for 16 hours, concentrated, and purified by silica gel chromatography (29:70:1 EtOAc/hexane/$Et_3N$) to provide 2.06 g (85%) of 10 as a viscous oil; TLC $R_f$ 0.35 (39:60:1 EtOAc/hexane/$Et_3N$).

5-O-benzoyl-6-O-(4',4"-dimethoxytriphenylmethyl)-1-O-(tert-butyldimethylsilyl)-1,5,6-hexanetriol, 11. To a solution of 2.06 g (3.8 mmol) of 10 in 19 mL of pyridine was added 532 mL (644 mg, 4.58 mmol) of benzoyl chloride, and the mixture was stirred for 20 hours and concentrated on the rotary evaporator to remove most of the pyridine keeping the bath temperature below 30° C. The mixture was partitioned between 50 mL of EtOAc and 50 mL of saturated $NaHCO_3$ solution. The EtOAc layer was washed with 50 mL of saturated $NaHCO_3$ solution, 25 mL of saturated NaCl solution, dried ($Na_2SO_4$), filtered, and concentrated. Purification by silica gel chromatography (10:89:1 EtOAc/hexane/$Et_3N$) provided 1.66 g of 11 as a viscous oil: TLC $R_f$ 0.27 (1:9 EtOAc/hexane); $^1$H NMR ($CDCl_3$) 0.5 (s, 6H), 0.87 (s, 9H), 1.40 (m, 2H), 1.56 (m, 2H), 1.82 (m, 2H), 3.28 (dd, 2H), 3.60 (t, 2H), 3.80 (s, 6H), 5.38 (m, 1H), 6.79 (m, 4H), 7.17–7.65 (m, 12H), 8.11 (d, 2H).

5-O-benzoyl-6-O-(4',4"-dimethoxytriphenylmethyl)-1,5,6-hexanetriol, 12. To a solution of 1.66 g (2.56 mmol) of 11 in 5.2 mL of THF under $N_2$ atmosphere was added 5.12 mL (5.12 mmol) of a 1M solution of tetrabutylammonium fluoride in THF. The mixture was stirred for 3 hours at ambient temperature and concentrated on the rotary evaporator. Purification by silica gel chromatography (1:1 EtOAc/hexane) provided 1.18 g (86%) of 12 as a viscous oil. Further purification was possible by preparative HPLC (12 mL/min, 9:1 MeOH/$H_2O$, 22.4 mm $C_{18}$): TLC $R_f$ 0.14 (1:1 hexane/EtOAc); $^1$H NMR ($CDCl_3$) 1.37 (m, 2H), 1.57 (m, 2H), 1.79 (m, 2H), 3.29 (dd, 2H), 3.60 (t, 2H), 3.75 (s, 6H), 5.36 (m, 1H), 6.80 (m, 4H), 7.17–7.60 (m, 12H), 8.12 (d, 2H).

O-5-benzoyloxy-6-O-(4',4"-dimethoxytriphenylmethyl) hexyl-O-(2'-cyanoethyl)-N,N-diisopropylphosphoramidite, 13. To a solution of 681 mg (1.26 mmol) of 12 and 111 mg (0.65 mmol) of diisopropylammonium tetrazolide in 6.5 mL of $CH_2Cl_2$ was added a solution of 417 mg (1.38 mmol) of O-cyanoethyl-N,N,N',N'-tetraisopropylphosphorodiamidite in 1.0 mL of $CH_2Cl_2$. The mixture was stirred for 2 hours and partitioned between 25 mL of $CH_2Cl_2$ and 25 mL of chilled saturated $NaHCO_3$ solution. The $CH_2Cl_2$ layer was washed with saturated NaCl solution, dried ($Na_2SO_4$), filtered, and concentrated. Purification by filtration through a 2" plug of basic alumina in a 25 mm column, eluting with 9:1 $CH_2Cl_2$/$Et_3N$ provided 798 mg of 13 as a viscous oil: $^1$H NMR ($CDCl_3$) 1.19 (m, 12H), 1.42 (m, 2H), 1.65 (m, 2H), 1.81 (m, 2H), 2.69 (m, 2H), 3.28 (dd, 2H), 3.57 (m, 4H), 3.78 (s, 6H) (underlying m, 2H), 5.40 (m, 1H), 6.79 (dd, 4H), 7.27–7.64 (m, 12H), 8.17 (d, 2H); $^{31}$P NMR ($CDCl_3$, 15% $H_3PO_4$ internal standard) 148.0; HRMS (FAB, MH$^+$), calc'd for $C_{43}H_{54}O_7N_2P_1$ 741.3669, found 741.3678.

Example 3

Preparation of O-(14-(4',4"-dimethoxytriphenylmethoxy)-7,8-dithiotetradecyl)-O-(2-cyanoethyl)-N-N-diisopropoylohosphoramidite FIG. 3 schematically shows the reaction scheme for this phosphoramidite. The details of the scheme are described below.

S-(6-hydroxyhexyl)isothiuronium chloride, 14. To a solution of 16.6 mL (20.0 g, 146 mmol) of 6-chlorohexanol in 49 mL of ethanol was added 11.1 g (146 mmol) of thiourea, and the mixture was refluxed for 24 hours. The mixture was cooled to 0° C., and the product crystallized. The crystals were collected by vacuum filtration and dried to give 28.4 g (92%) of 14 as a white solid: mp 122°–124° C.; $^1$H NMR (DMSO) 1.40 (m, 4H), 1.65 (m, 2H), 3.21 (t, 2H) 3.41 (t, 2H), 9.27 and 9.33 (overlapping broad singlets, 4H).

6-Mercaptohexan-1-ol, 15. To a solution of 17.8 mg (83.6 mmol) of 14 in 120 mL of $H_2O$ and 120 mL of EtOH was added 9.25 g of NaOH pellets. The mixture was refluxed for 4 hours. The mixture was carefully concentrated to approximately 75 mL, and the concentrate was purified by vacuum distillation to provide 7.4 g (66%) of 15: bp 95°–105° C. @ 5 mm Hg; $^1$H NMR ($CDCl_3$) 1.41 (m, 9H) 2.59 (dt, 2H), 3.69 (t with underlying brd s, 3H).

Bis-(6-hydroxyhexyl)disulfide, 16. To a solution of 4.26 g (31.7 mmol) of 15 in 10 mL of MeOH and 13.7 mL (9.97 g, 98.5 mmol) of $Et_3N$ under $N_2$ atmosphere and cooled in an ice bath was added dropwise over 10 min a solution of 4.02 g (15.8 mmol) of $I_2$ in 90 mL of MeOH. The cooling bath was removed, and the mixture was stirred at ambient temperature for 4 hours. The mixture was concentrated on the rotary evaporator and purified by silica gel chromatography (1:1 hexane/EtOAc) to provide 3.12 g (73%) of 16 as a pale yellow solid: TLC $R_f$ 0.18 (1:1 hexane/EtOAc); mp 38°–48° C.; $^1$H NMR ($CDCl_3$) 1.15–2.20 (m, 16H), 2.73 (t, 4H), 3.70 (t, 4H).

Mono-O-(4',4"-dimethoxytriphenylmethyl)-bis-(6-hydroxyhexyl)disulfide, 17. To a solution of 3.12 g (11.7 mmol) of 16 and 45 mL of pyridine was added 3.97 g (11.7 mmol) of 4,4'-dimethoxytriphenylmethyl chloride, and the mixture was stirred at ambient temperature for 16 hours. Most of the pyridine was removed on the rotary evaporator, and the residue was partitioned between 100 mL of saturated $NaHCO_3$ solution and 100 mL of EtOAc. The EtOAc layer was washed with 50 mL of saturated NaCl solution, dried ($Na_2SO_4$), filtered and concentrated to an oil. Purification by silica gel chromatography (9:1 $CH_2Cl_2$/EtOAc) yielded 2.84 g (43%) of 17 as a viscous oil: TLC $R_f$ 0.35 (9:1 $CH_2Cl_2$/EtOAc); $^1$H NMR ($CDCl_3$) 1.41 (m, 8H), 1.65 (m, 8H), 2.70 (two overlapping triplets, 4H), 3.08 (t, 2H), 3.65 (t, 2H), 3.81 (s, 6H), 6.85 (d, 4H), 7.32 (m, 7H), 7.47 (d, 2H).

O-(14-(4',4"-Dimethoxytriphenylmethoxy)-7,8-dithiotetradecyl)-O-(2-cyanoethyl)-N,N-diisopropylphosphoramidite, 18. To a solution of 771 mg (1.36 mmol) of 17 and 116 mg (0.68 mmol) of diisopropylammonium tetrazolide in 6.8 mL of $CH_2Cl_2$ under $N_2$ atmosphere was added a solution of 458 mg (1.52 mmol) of O-cyanoethyl-N,N,N',N'-tetraisopropylphosphorodiamidite in 0.5 mL of $CH_2Cl_2$. The mixture was stirred for 4 h and partitioned between 25 mL of $NaHCO_3$ and 3×25 mL of $CH_2Cl_2$. The combined $CH_2Cl_2$ layers were washed with saturated NaCl solution, dried ($Na_2CO_3$), filtered and concentrated to an oil. Purification by filtration through a 2" plug of basic alumina in a 25 mm column, eluting with 9:1 $CH_2Cl_2/Et_3N$ provided 831 mg (80%) of 18 as a viscous oil; $^1H$ NMR ($CDCl_3$) 1.25 (m, 12H), 1.45 (m, 8H), 1.70 (m, 8H), 2.72 (m, 6H), 3.09 (t, 2H), 3.65 (m, 4H), 3.87 (s, 6H), 3.91 (m, 2H), 6.89 (d, 4H), 7.35 (m, 7H), 7.49 (d, 2H); $^{31}P$ NMR ($CDCl_3$ with 15% $H_3PO_4$ internal standard) 147.69; HRMS (FAB, MH$^+$) calc'd for $C_{42}H_{62}N_2O_5P_1S_2$ 769.3839, found 769.3853.

Example 4

Addition of Phosphoramidite of Example 1 to Oligonucleotide

A fivefold molar excess (760 mg) of the phosphoramidite of Example 1 was coupled to the 5' end of an oligonucleotide which was attached to 10 g (300 μmoles) CPG (control pore glass) support. This synthesis was performed on a Milligen 8800 DNA synthesizer using the manufacturer's protocols for DNA synthesis.

In a separate instance, in a 1 μmole scale reaction on a Pharmacia Gene-Assembler DNA synthesizer, the coupling efficiency was determined to 96% by trityl release. For this determination, the phosphoramidite from Example 3 was used.

After the reaction, the CPG was suspended in 100 ml concentrated ammonia and kept at 55° C. overnight. After filtration, the deprotected oligonucleotide was purified by sodium chloride gradient and ion-exchange chromatography.

The fractions were analyzed by polyacrylamide gel electrophoresis and the product containing fractions pooled, adjusted to 0.3M NaCl with 3M NaCl solution and precipitated by the addition of an equal volume of cold isopropanol. The product was collected by centrifugation and dried in vacuo.

The pellet was then dissolved in 40 ml water and oxidized by treatment with a fivefold molar excess of sodium metaperiodate (83.6 mg for 2 g purified oligonucleotide in this example) at 0° C. for 30 min. The solution was again adjusted to 0.3M NaCl and precipitated as above to remove the formaldehyde produced in this reaction. After centrifugation and drying, this material was used in the next step.

Example 5

Conjugation of Oligonucleotide of Example 4 to D-glutamic acid, D-lysine (DEK) Polymer 100 mg of oxidized oligonucleotide (2.5 μmoles) was dissolved in 1.33 ml of 100 mM $NaBO_3$, pH 8.0. Then, 2.5 mg of DEK (0.25 μmoles, MWt 10,000, 60:40 weight ratio of D-glutamic acid to D-lysine) and 0.79 mg $NaCNBH_3$ (12.5 μmoles) was added. The mixture (2.0 ml) was incubated at 37° C. for 3 days. The condensation product was purified by S-200 (Pharmacia, Uppsala, Sweden) chromatography.

The fractions were labeled with alpha $^{32}p$ ddATP and terminal transferase for viewing on a standard 8% DNA sequencing polyacrylamide gel.

Figure 4:
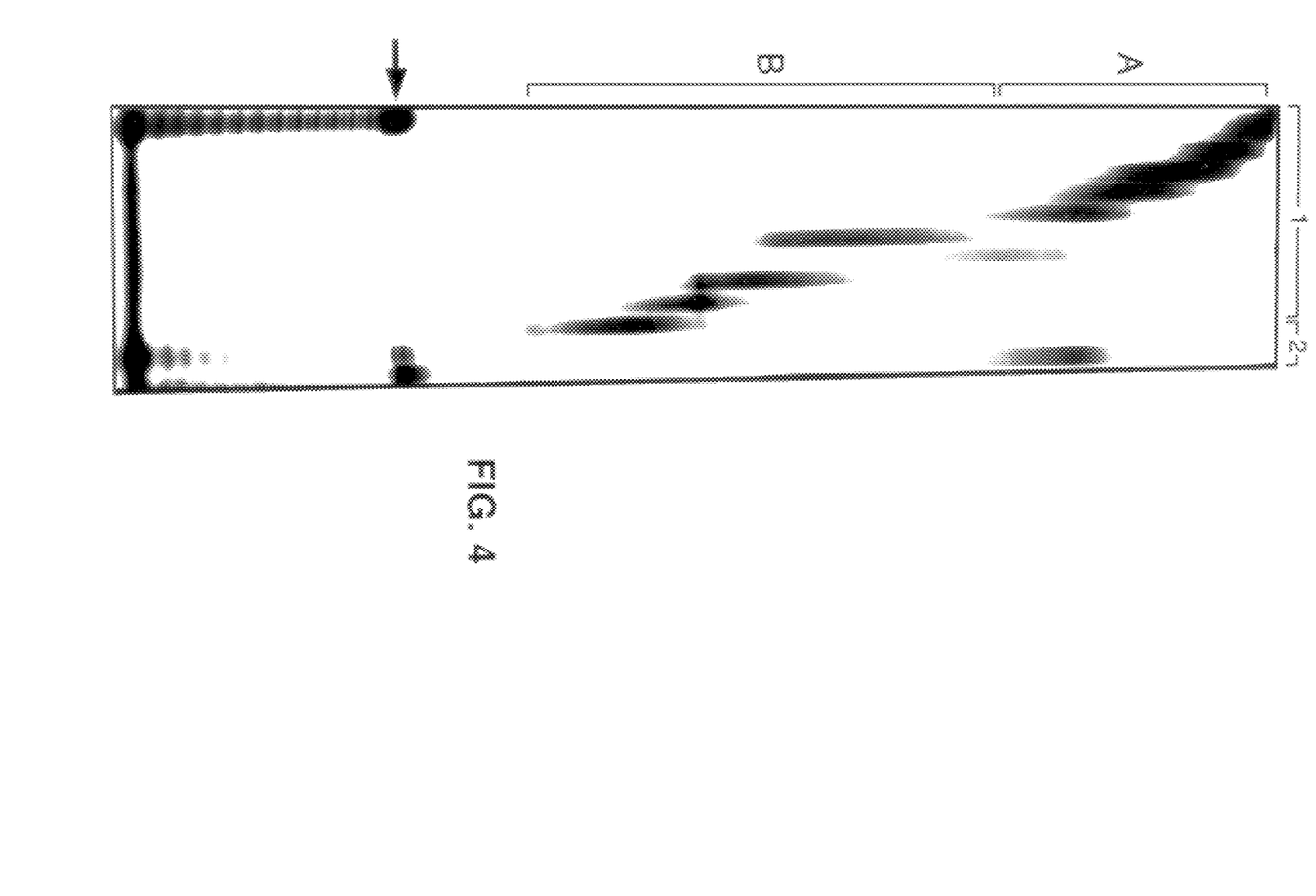
FIGS. 4 and 5 are autoradiograms of the gels described in Examples 5 and 6.

The various radiolabeled fractions were visualized by electrophoresis and autoradiography as presented in FIG. 4. The lanes labeled "2" contain unconjugated full length oligonucleotide and the arrow indicates the position of the 50-mer. Lanes labeled "1" contain conjugates of decreasing molecular weight.

Example 6

Conjugation of Oligonucleotide of Example 4 to Keyhole Limpet Hemocyanin (KLH)

Figure 5:
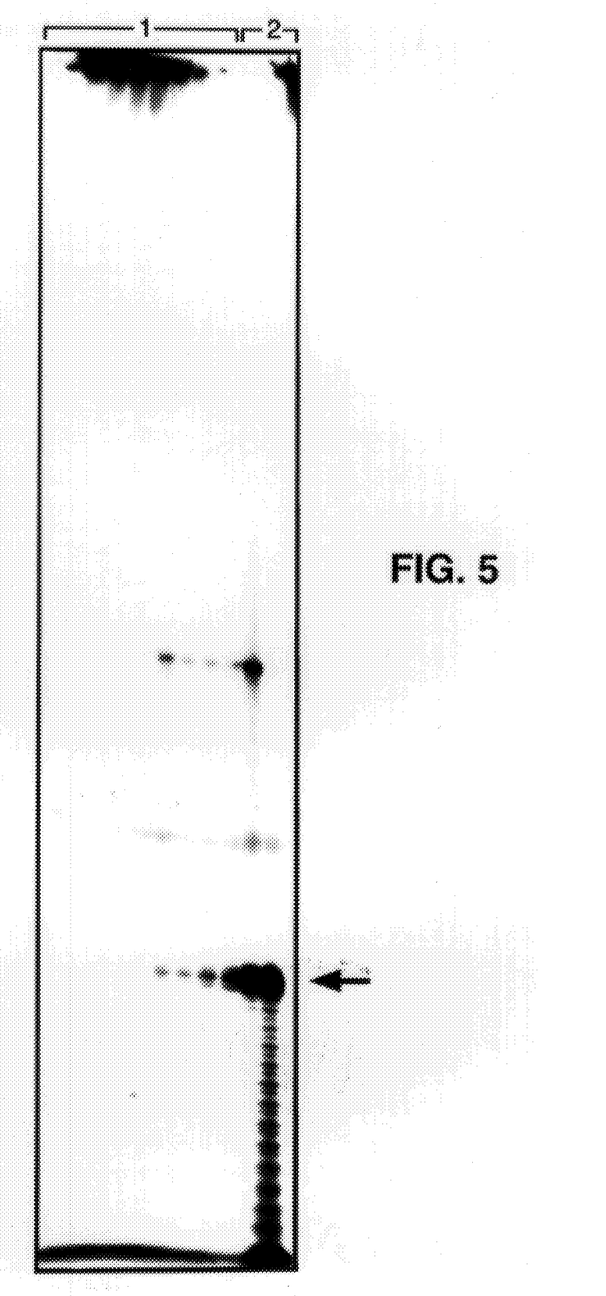

100 mg crude oxidized oligonucleotide (2.5 μmoles) was dissolved in 1.33 ml of 50 mM $NaBO_3$, pH 8.0. Then, 31.3 mg of KLH (0.208 μmoles) and 2.0 mg $NaCNBH_3$ (31.8 μmoles) was added. The mixture (2.0 ml) was incubated at 37° C. for 3 days. The condensation product was purified by S-200 chromatography. The various fractions were radiolabeled using the same process as described above for D-EK and were then visualized after electrophoresis and autoradiography as presented in FIG. 5. Lanes labeled "1" are high molecular weight conjugates, lanes labeled "2" contain mostly unconjugated oligo and the arrow indicates the position of the 50-mer. Modifications of the above-describes modes for carrying out the invention that are obvious to those of ordinary skill in the fields of organic chemistry, and particularly oligonucleotide synthesis and derivatization are intended to be within the scope of the following claims. The fractions which contained the oligo-KLH conjugate were pooled for subsequent annealing to the complimentary oligonucleotide strand to construct a double-stranded DNA-KLH conjugate.

Example 7

Preparation of Acetal-Protected Diol Phosphoramidite 4-(4-hydroxy-1-butyl)-2-phenyl-1,3 dioxolane.

A mixture of 1,2,6-trihydroxyhexane (2.58 g) and benzaldehyde dimethyl acetal (3.18 g) is treated with toluene sulfonic acid hydrate (2.08 g). The mixture is allowed to stir at room temperature for 60 hours, and is then partitioned between saturated aqueous sodium bicarbonate (50 ml) and methylene chloride (20 ml). The benzaldehyde dimethyl acetal (3.18 g) is treated with toluene sulfonic acid hydrate (2.08 g). The mixture is allowed to stir at room temperature for 60 hours, and is then partitioned between saturated aqueous sodium bicarbonate (50 ml) and methylene chloride (20 ml). The layers are separated, the aqueous layer is re-extracted with methylene chloride, the organic layers are dried over anhydrous sodium sulfate, filtered, and concentrated to an oil (2.66 g), which is purified by column chromatography (silica gel, 1:1 ethyl acetate/hexanes). Pooling and concentrating the appropriate fractions give the title compound as an oil (1.19 g): TLC Rf=0.18 (silica, 1:1 ethyl acetate/hexanes); $^1H$ NMR ($CDCl_3$), δ, 1.62 (m, 6H), 3.67 (m, 3H), 3.25 (m, 2H), 6.37 (s, 0.6H), 6.50 (s, 0.4H), 8.04 (br. s, 5H).

In a similar manner, but beginning with benzaldehyde in place of benzaldehyde dimethyl acetal, the title compound is also obtained.

(4-(2-phenyl-1,3-dioxol-4-yl) butyl)-O-(2-cyanoethyl)-N-N-diisopropylphosphoramidite. A solution of the above dioxolane (1.19 g), and diisopropylamine (2.0 ml) in methylene chloride (22 ml) is treated with cyanoethyldiisopropylchlorophosphoramidite (0.92 ml) and allowed to stir at 24° C. for 1.5 hours. The mixture is partitioned between saturated aqueous sodium bicarbonate (25 ml) and methylene chloride (25 ml). The layers are separated, the aqueous layer is re-extracted with methylene chloride, the organic layers are dried over anhydrous sodium sulfate, filtered, and concentrated to an oil (2.13 g), which is purified by column chromatography (basic alumina, 1:1 methylene chloride/ hexanes, 1% triethylamine). Pooling and concentrating the appropriate fractions gives the title compound as an oil (1.28 g): $^1$H NMR (CDCl$_3$), δ, 1.13 (12H), 1.5–1.9 (m, 8H), 2.58 (q, 2H), 3.5–3.8 (m, 8H), 4.0–4.3 (m, 2H), 5.8 (s, 0.6H), 5.92 (s, 0.4H), 7.3–7.5 (m, 5H).

In a similar manner, the following phosphoramidites are prepared:
(4-(2-methoxyphenyl-1,3-dioxol-4-yl) butyl)-O-(2-cyanoethyl)-N-N-diisopropylphosphoramidite;
(4-(2-p-butylphenyl-1,3-dioxol-4-yl) butyl)-O-(2-cyanoethyl)-N-N-diisopropylphosphoramidite;
(4-(2-biphenyl-1,3-dioxol-4-yl) butyl)-O-(2-cyanoethyl)-N-N-diisopropylphosphoramidite;
(4-(2-methyl-2-phenyl-1,3-dioxol-4-yl) butyl)-O-(2-cyanoethyl)-N-N-diisopropylphosphoramidite.

Example 8

Addition of Phosphoramidite of Example 7 to Oligonucleotide

In the manner of Example 4, the phosphoramidite of Example 7 is coupled to the oligonucleotide. Following purification, the acetal protecting group is removed with 80% acetic acid/water for 40 minutes. The progress of the reaction is monitored by HPLC using a Gen Pak Fax column (Waters Associates), using 0.5M sodium phosphate at pH 7.5, with a 1.0M sodium chloride/10% methanol gradient. The starting acetal elutes at 20.1 minutes, and the hydrolyzed diol elutes at 18.9 minutes.

Modifications of the above-described modes for carrying out the invention that are obvious to those of skill in the fields of organophosphorous chemistry, nucleotide chemistry, oligonucleotide synthesis, or related fields are intended to be within the scope of the following claims.

We claim:

1. A 5'-modified oligonucleotide of the formula:

where (O.N.) represents an oligonucleotide chain, X is a chalcogen atom of atomic number 8 to 16, inclusive, $X^1$ is $O^-$, methyl, —OCH$_3$ or NR$^1$R$^2$ where R$^1$ and R$^2$ are individually hydrogen or alkyl of 1 to 6 carbon atoms, G is a hydrocarbylene group of 1 to 20 carbon atoms and Z is a hydroxy-protected vicinal diol group bound to G by a vicinal diol carbon atoms or a disulfide group bound to G by one of the sulfur atoms of the disulfide group wherein said 5'-modified oligonucleotide is not attached to a solid substrate.

2. The 5'-modified oligonucleotide of claim 1 wherein Z is where R$^3$ and R$^4$ are individually hydrogen, alkyl of 4 to 20 carbon atoms or monocyclic aryl of 6 to 20 carbon atoms, and Y$^1$ and Y$^2$ are individual hydroxy protecting groups or are joined by a single-atom bridge to form a five-membered ring protecting group, or where R$^5$ is an alkylene group of 4 to 20 carbon atoms or a monocyclic arylene group of 6 to 20 carbon atoms and Y$^3$ is a hydroxy-protecting group.

3. The 5'-modified oligonucleotide of claim 2 wherein Z is and Y$^1$ and Y$^2$ are removed to leave free hydroxy groups.

4. The 5'-modified oligonucleotide of claim 1 wherein G is —(CH$_2$)$_4$—, and Z is where Y$^1$ and Y$^2$ are benzoyl.

5. The 5'-modified oligonucleotide of claim 4 wherein Y$^1$ and Y$^2$ are removed to leave free hydroxyl groups.

6. The 5'-modified oligonucleotide of claim 1 wherein G is —(CH$_2$)$_4$— and Z is where Y$^1$ is benzoyl and Y$^2$ is dimethoxytrityl.

7. The 5'-modified oligonucleotide of claim 1 wherein Z is wherein R$^6$ and R$^7$ are individually hydrogen, aryl or substituted aryl of 6 to 30 carbon atoms, alkyl of 1 to 20 carbon atoms or aromatic-substituted alkyl of less than 30 carbon atoms, with the proviso that both R$^6$ and R$^7$ are not hydrogen.

8. The 5'-modified oligonucleotide of claim 7 wherein R$^6$ and R$^7$ are individually hydrogen or phenyl optionally substituted with alkyl of 1 to 8 carbons, alkoxy of 1 to 8 carbons, 1 to 4 halogen atoms of atomic number 9 to 35, nitro-, or phenyl, with the proviso that both R$^6$ and R$^7$ are not hydrogen.

9. The 5'-modified oligonucleotide of claim 7 wherein R$^6$ is hydrogen and R$^7$ is phenyl, p-butylphenyl, p-methoxyphenyl, p-t-butylphenyl or biphenyl.

10. The 5'-modified oligonucleotide of claim 1 wherein G is —(CH$_2$)$_6$—, and Z is where $R^5$ is —$(CH_2)_6$— and $Y^3$ is dimethoxy trityl.

11. The 5'-modified oligonucleotide of claim 3 wherein Z is oxidized to form a terminal aldehyde group on the oligonucleotide.

12. The 5'-modified oligonucleotide of claim 10 wherein Z is reduced to form a terminal thiol group on the oligonucleotide.

13. A conjugate of an amino group-containing carrier molecule and the 5'-modified oligonucleotide of claim 11 wherein the conjugate is formed by reaction between said amino group and said terminal aldehyde group.

14. The conjugate of claim 13 wherein the carrier molecule is a polymer.

15. The conjugate of claim 14 wherein the polymer is an amino acid polymer.

16. A conjugate of a carrier molecule having a functional group and the 5'-modified oligonucleotide of claim 12 wherein the conjugate is formed by reaction between said group and said terminal thiol group.

17. The conjugate of claim 16 wherein the carrier is a polymer.

18. The 5'-modified oligonucleotide of claim 1 wherein G is —$(CH_2)_6$—, and Z is

—S—S—$R^5$—O—$Y^3$ where $R^5$ is —$(CH_2)_6$— and $Y^3$ is trityl.

* * * * *

UNITED STATES PATENT AND TRADEMARK OFFICE

CERTIFICATE OF CORRECTION

PATENT NO. : 5,874,552

DATED : February 23, 1999

INVENTOR(S) : David S. Jones, John P. Hachmann, Michael J. Conrad, Stephen Coutts and Douglas A. Livingston It is certified that error appears in the above-identified patent and that said Letters Patent is hereby corrected as shown below:

Claim 3, line 6, after "oligonucleotide" please delete --.--.

Signed and Sealed this

Eighteenth Day of May, 1999

Attest:

Q. TODD DICKINSON

*Attesting Officer*  Acting Commissioner of Patents and Trademarks

UNITED STATES PATENT AND TRADEMARK OFFICE
CERTIFICATE OF CORRECTION

PATENT NO.    : 5,874,552
DATED         : February 23, 1999
INVENTOR(S)   : David S. Jones et al.

It is certified that error appears in the above-identified patent and that said Letters Patent is hereby corrected as shown below:

Drawings,
Sheet 3, Figure 3, the portion of compound 16 reading "ODMT" should read -- OH --.

Column 14,
Line 6, after "oligonucleotide" please delete " . ".

Signed and Sealed this

Eighth Day of July, 2003

JAMES E. ROGAN
*Director of the United States Patent and Trademark Office*